US00PP31846P2

(12) United States Plant Patent
Holtmaat

(10) Patent No.: US PP31,846 P2
(45) Date of Patent: Jun. 2, 2020

(54) ***MONARDA* PLANT NAMED 'MONBEBR'**

(50) Latin Name: ***Monarda* Hybrid**
Varietal Denomination: Monbebr

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 16/602,344

(22) Filed: Sep. 18, 2019

(30) Foreign Application Priority Data

Aug. 7, 2019 (QZ) ..... PBR 2019/1931

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Monarda* plant named 'Monbebr' that is characterized by its relatively short plant height, its strong stems, its flowers that are white in color, and its good resistance to powdery mildew (*Sphaerotheca pannosa* var. *rosa*) under the conditions tested.

2 Drawing Sheets

Botanical classification: *Monarda* Hybrid.
Variety denomination: 'Monbebr'.

CROSS REFERENCE TO A RELATED APPLICATION

This application claims priority to European Community Plant Variety Office (CPVO) Plant Breeder's Rights Application No. 2019/1931 filed on Aug. 7, 2019, the entire contents of which is incorporated by reference herein.

BACKGROUND OF THE INVENTION

The present invention relates to a new and distinct cultivar of *Monarda*. The new cultivar will be referred to hereafter by its cultivar name, 'Monbebr'. 'Monbebr' is a new variety of bee balm suitable for landscape plantings.

The new cultivar derived from a breeding program conducted by the Inventor at a nursery in Zuidwolde, The Netherlands. 'Monbebr' was discovered in June of 2017 by the Inventor from amongst seedlings in a trial field that had been planted with seed collected from numerous plants from the Inventor's breeding program. The exact parentage is therefore unknown.

Asexual propagation of the new cultivar was first accomplished under the direction of the Inventor by tissue culture using meristematic tissue in September 2018 in Heerhugowaard, The Netherlands. Asexual propagation by tissue culture and softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Monbebr' as a unique cultivar of *Monarda*.

1. 'Monbebr' exhibits a relatively short plant height.
2. 'Monbebr' exhibits strong stems.
3. 'Monbebr' exhibits flowers that are white in color.
4. 'Monbebr' exhibits good resistance to powdery mildew (*Sphaerotheca pannosa* var. *rosa*) under the conditions tested.

'Monbebr' can be compared to the *Monarda* cultivars 'Schneewittchen' (U.S. Plant Pat. No. 28,573) and 'Sioux' (not patented). 'Schneewittchen' and 'Sioux' are both similar to 'Monbebr' in having flowers that are white in color. 'Schneewittchen' differs from 'Monbebr' in having a taller plant height and in being more prone to powdery mildew. 'Sioux' differs from 'Monbebr' in having a taller plant height and flowers that are white in color with hints of purple, and in being more prone to powdery mildew.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website listing by AB Cultivars; a company owned by the Inventor.

BRIEF DESCRIPTION OF THE DRAWINGS

The accompanying colored photographs illustrate the overall appearance and distinct characteristics of one-year-old plants of the new *Monarda* as grown outdoors in 17-cm containers in Zuidwolde, The Netherlands.

Figure 1:
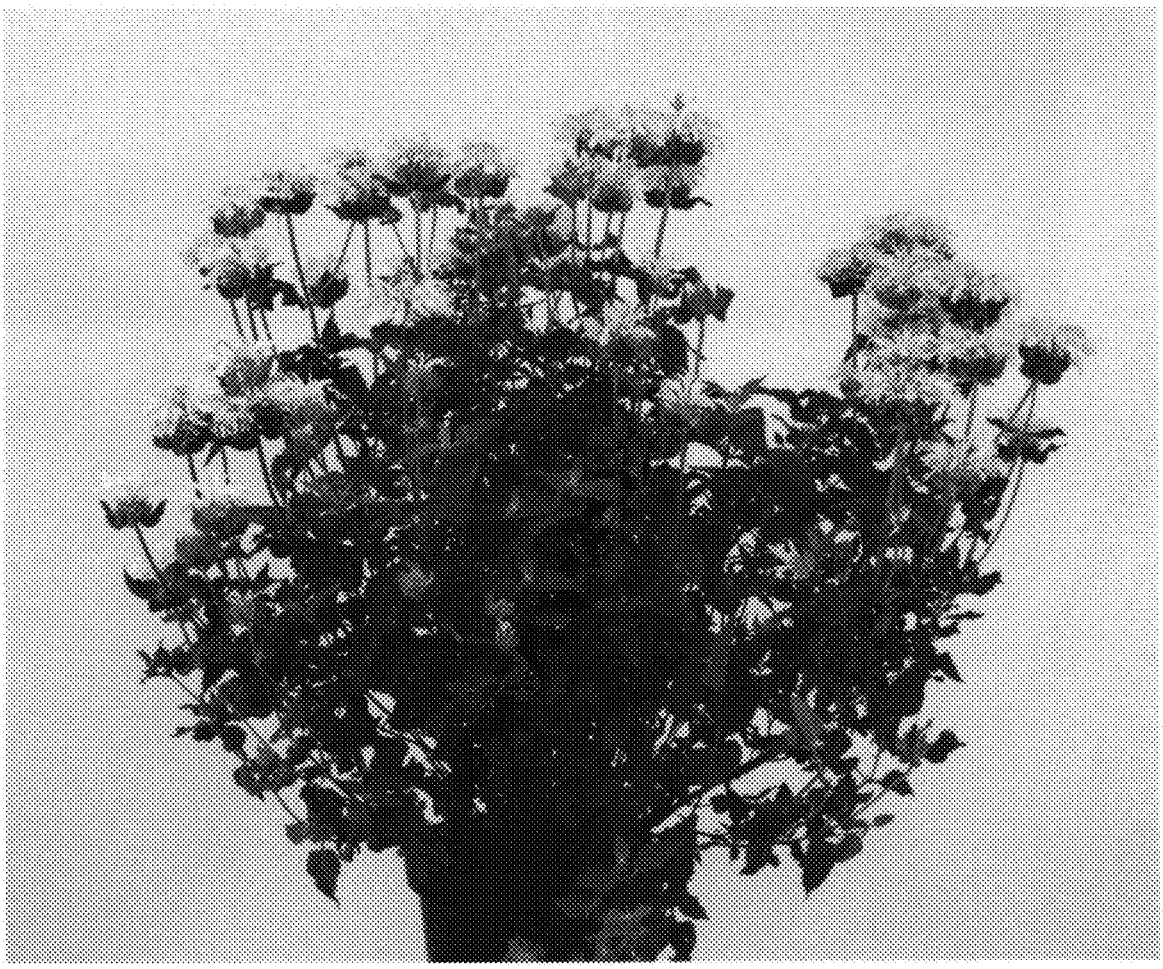
FIG. 1 provides a view of the plant habit of 'Monbebr' in bloom.
Figure 2:
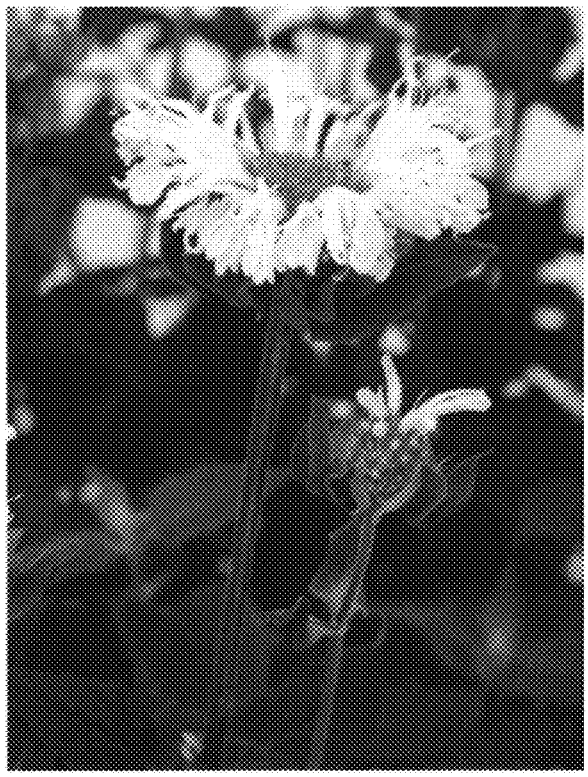
FIG. 2 provides a view of an inflorescence of 'Monbebr'.
Figure 3:
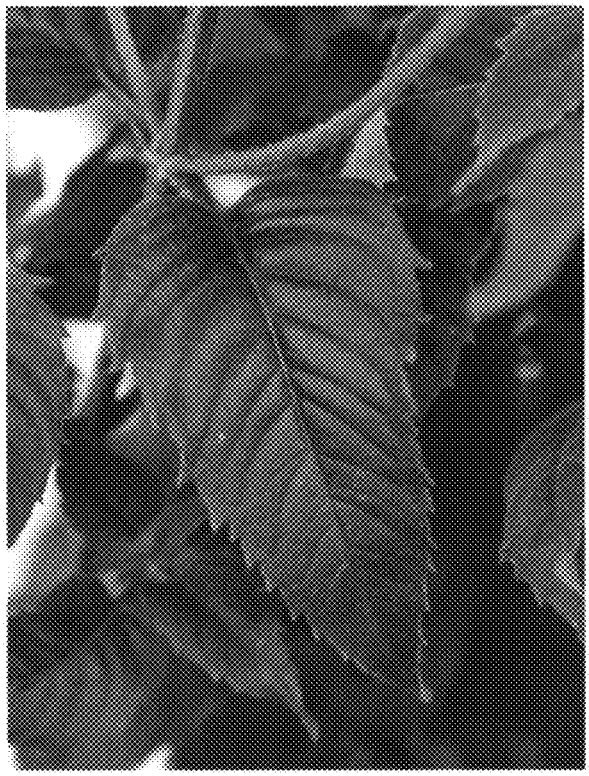
FIG. 3 provides a close-up view of a leaf of 'Monbebr'.

The colors in the photographs are as close as possible with digital photography techniques available, the color values cited in the detailed botanical description accurately describe the colors of the *Monarda*.

DETAILED BOTANICAL DESCRIPTION

The following is a detailed description of one-year-old plants of the new cultivar as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—12 weeks, from mid-June to late September in The Netherlands.

*Plant type*.—Perennial.

*Plant habit*.—Upright, broadly spreading, compact.

*Plant shape*.—Broad obovate to flattened globular.

*Height and spread*.—Reaches an average of 47.5 cm in height (soil level to top of foliar plane), 60 cm in height (soil level to top of floral plane) and 60 cm in width.

*Hardiness*.—At least in U.S.D.A. Zones 5 to 9.

*Diseases and pests*.—Good resistance has been observed to powdery mildew (*Sphaerotheca pannosa* var. *rosa*), no resistance or susceptibility to pests has been observed.

*Root description*.—Fine and fibrous.

*Propagation*.—Tissue culture and softwood stem cuttings.

*Root development*.—An average of 3 weeks for root initiation with a young rooted plant produced in an average of 2 months.

*Growth rate and vigor*.—Moderate.

Stem description:

*Stem shape*.—Quadrangular.

*Stem color*.—Young; 144B, mature; 144A, old wood; semi-woody stem bases 200A and N200A.

*Stem surface*.—Young stems; slightly glossy and moderately to densely covered with short thin hairs; an average of 1 mm in length and NN155D in color, mature stems glabrous and slightly glossy, base; smooth barked.

*Stem aspect*.—Main branches average of 20° to vertical (varying between 0° and 40°), lateral branches average of 45° to main branches.

*Stem strength*.—Strong.

*Stem size*.—Average of 45.7 cm in length (excluding inflorescence), 4 mm in diameter.

*Branching*.—Growing from base, average of 60 main branches, Average of 2 lateral branches per main branch.

*Internode length*.—Average of 4.6 cm.

*Fragrance*.—Strongly aromatic fragrance.

Foliage description:

*Leaf shape*.—Narrow deltoid to ovate.

*Leaf division*.—Simple.

*Leaf base*.—Truncate.

*Leaf apex*.—Long acuminate.

*Leaf venation*.—Pinnate, color upper surface 148A, color lower surface 148B.

*Leaf margins*.—Coarsely serrate.

*Leaf attachment*.—Petiolate.

*Leaf arrangement*.—Opposite.

*Leaf size*.—Average of 7.5 cm in length and 4.4 cm in width.

*Leaf color*.—Young upper surface; 137B and 143A, young lower surface; 138A, mature upper surface; 147A and N189A, mature lower surface; 147A.

*Leaf surface*.—Upper surface slightly glossy, non-rugose, lower surface is very slightly glossy, slightly rugose, both surfaces densely pubescent with short strigose hairs; an average of 1 mm in length and 156D in color, both surfaces moderately soft to touch.

*Petioles*.—Average of 1.3 cm in length, flattened, 3 mm in width, strong, upper surface color; between 148A and 197A, lower surface color; 148A, upper surface glabrous and matte, lower surface slightly glossy and densely covered with strigose hairs; average of 1 mm in length and 156D in color.

*Fragrance*.—Strongly aromatic fragrance, pleasant and spicy.

Inflorescence description:

*Inflorescence type*.—Terminal and axillary globular spikes.

*Inflorescence number*.—1 per terminus and lateral stem.

*Inflorescence fragrance*.—None.

*Inflorescence size*.—Average of 5.3 cm in height and 7.4 cm in diameter.

*Inflorescence aspect*.—Upright to outward.

*Inflorescence habit*.—Freely flowering, self-cleaning.

*Peduncles*.—None, globular spikes sessile to stem.

*Floret buds*.—Narrowly oblanceolate and curved, average of 2.3 cm in length and 3.5 mm in width prior to opening, 155A in color, base NN155D, immature calyx 144B and changing to 145D at the base, surface is matte and densely pubescent with very short glandular pubescence; an average of 7.5 mm in length and NN155D in color.

*Floret longevity*.—Average of one week.

*Floret type*.—Labiate.

*Floret quantity*.—Average of 175 per inflorescence, over 20,000 per plant.

*Floret size*.—Average of; 1.9 cm in height, 7 mm in diameter, 3.5 cm in depth, 2 mm throat diameter, tube; 1.8 cm in length and 2.5 mm in diameter.

*Sepals*.—5 per flower, 1 whorl, 90% fused into tube, 1 cm in length, 0.5 mm in width, narrow, oblong and fused into tubular shape, free mucronate tip, free part of margins entire, upper surface matte and smooth, densely covered in pubescence at top margins, average of 0.5 mm in length, NN155D in color, lower surface is matte, glabrous and smooth, color; upper and lower surface when opening 144B, changing to 145D, veined 144B, upper surface and lower surface when fully open; 143C, changing to 145C at the base, veined 144B.

*Petals*.—A average of 2 per flower (1 upper and 1 lower petal), 1 whorl, lower 60% fused into tube, 3 mm in length, upper petal 1 mm in width, lower petal width 7 mm, upper petal shape is lanceolate, lower petal shape is oblanceolate, upper petal tip is narrow acute, lower petal tip is 3-lobed, lateral lobes with an obtuse apex, central lobe with an emarginate apex, entire margins, lower petal moderately undulate, upper surface is smooth, glabrous and slightly velvety, lower surface and flower tube are very slightly velvety and densely pubescent with very short glandular pubescence; an average of 0.5 mm in length and NN155D in color, tube throat surface is smooth and glabrous, color; upper and lower surface when opening and fully open are NN155D in color.

*Calyx*.—Rotate, tubular, average of 1 cm in length, 3 mm in diameter.

*Floral bracts*.—Average of 20, up to 2.3 cm in length and 1.4 cm in width, ovate to lanceolate in shape, apex cuneate, base auriculate, both surfaces velvety and soft, lower surface covered with soft pubescence an average of 0.4 mm in length.

Reproductive organs:

*Gynoecium*.—Pistil; 1, 3.5 cm in length, style; 3.4 cm in length, NN155A in color and changing to NN155D at the base, stigma; unequally cleft, 1 mm in diameter, NN155A in color, ovary; 157D in color.

*Androecium*.—Stamens; 2, filaments; 1.5 cm in length, NN155D in color, anther; dorsifixed and narrow elliptic in shape, 1.5 mm in length, 1 mm in width, 181C in color, pollen; low in quantity and 158D in color.

*Fruit/seed*.—None observed.

It is claimed:

1. A new and distinct cultivar of *Monarda* plant named 'Monbebr' as herein illustrated and described.

* * * * *